United States Patent [19]

Asayama et al.

[11] Patent Number: 4,657,640
[45] Date of Patent: Apr. 14, 1987

[54] METHOD OF SENSING AIR-TO-FUEL RATIO SENSOR OF AN ENGINE

[75] Inventors: Yoshiaki Asayama, Himeji; Seiya Kominami, Takasago, both of Japan

[73] Assignee: Mitsubishi Denki Kabushiki Kaisha and NGK Spark Plug Co., Ltd., Japan

[21] Appl. No.: 770,655

[22] Filed: Aug. 28, 1985

Related U.S. Application Data

[62] Division of Ser. No. 606,926, May 4, 1984.

[30] Foreign Application Priority Data

May 11, 1983 [JP] Japan ................. 58-83587

[51] Int. Cl.[4] .......................................... G01N 27/46
[52] U.S. Cl. ...................... 204/1 T; 204/425; 204/426
[58] Field of Search ................. 204/15, 421–429

[56] References Cited

U.S. PATENT DOCUMENTS

| | | | |
|---|---|---|---|
| 3,654,112 | 4/1972 | Beekmans et al. | 204/1 S |
| 3,691,023 | 9/1972 | Ruka et al. | 204/425 |
| 3,699,032 | 10/1972 | Rapp | 204/1 S |
| 4,272,329 | 6/1981 | Hetrick et al. | 204/425 |
| 4,391,691 | 7/1983 | Linder et al. | 204/425 |
| 4,472,262 | 9/1984 | Kondo et al. | 204/426 |
| 4,505,806 | 3/1985 | Yamada | 204/425 |

*Primary Examiner*—T. Tung
*Attorney, Agent, or Firm*—Leydig, Voit & Mayer

[57] ABSTRACT

A method to accurately sense the stoichiometric air-to-fuel (A/F) ratio by maintaining the electromotive force of an oxygen sensor at a predetermined value of about 100 mV and using an oxygen concentration measuring device of the solid electrolyte oxygen pumping type.

1 Claim, 3 Drawing Figures

METHOD OF SENSING AIR-TO-FUEL RATIO SENSOR OF AN ENGINE

BACKGROUND OF THE INVENTION

This invention is a Divisional Application of U.S. Ser. No. 606,926, filed May 4, 1984.

The present invention relates to a measuring device used to sense an air-to-fuel (A/F) ratio by measuring oxygen concentration in exhaust gases for an internal combustion engine, and more particularly to improvements in A/F ratio sensor of oxygen pumping type with ionically conducting solid elecyrolyte.

It is heretofore well known to control, for example, an engine of a vehicle to operate by stoichiometric air-to-fuel ratio by sensing the combustion state of fuel at the stoichiometric air-to-fuel (A/F) ratio by means of variations of an electromotive force produced due to the difference between the partial pressure of the oxygen of exhaust gas and the partial pressure of the oxygen of air with an oxygen sensor composed of ionically conducting solid electrolyte (e.g., stabilized zirconia). This oxygen sensor can produce a large variation output when the A/F of the ratio of air to fuel by weight is 14.7 of stoichiometric A/F, but produces almost no variation output in other operating air-to-fuel ratio. In case that the engine is operated at an air-to-fuel ratio other than the stoichiometric A/F, the output of the above oxygen sensor could not be utilized.

An oxygen concentration measuring device of the solid electrolyte oxygen pumping type has been proposed for enabling the sensing of air-to-fuel ratios in a wide range as disclosed in U.S. Pat. No. 4,272,329 (Japanese Patent Application Laid-open No. 130649/1981). However, this device cannot accurately sense the stoichiometric A/F.

SUMMARY OF THE INVENTION

An object of the present invention is to provide an air-to-fuel ratio sensor for an engine which is capable of accurately sensing the stoichiometric air-to-fuel ratio and of also sensing an air-to-fuel ratio larger than the stoichiometric air-to-fuel ratio.

According to the present invention, there is provided an air-to-fuel ratio sensor for an engine which comprises a solid electrolyte oxygen pump for controlling the partial pressure of oxygen in an air gap for introducing exhaust gas of the engine, a solid electrolyte oxygen sensor for generating an electromotive force corresponding to the partial pressure of the oxygen in the air gap and the partial pressure of the oxygen in the exhaust gas other than the air gap, means for controlling the current of the oxygen pump to hold the electromotive force produced by the oxygen sensor at a predetermined value, and means for holding the electromotive force of the oxygen sensor at a predetermined value higher than 100 mV.

DETAILED DESCRIPTION OF THE PREFERRED EMBODIMENT

Figure 1:
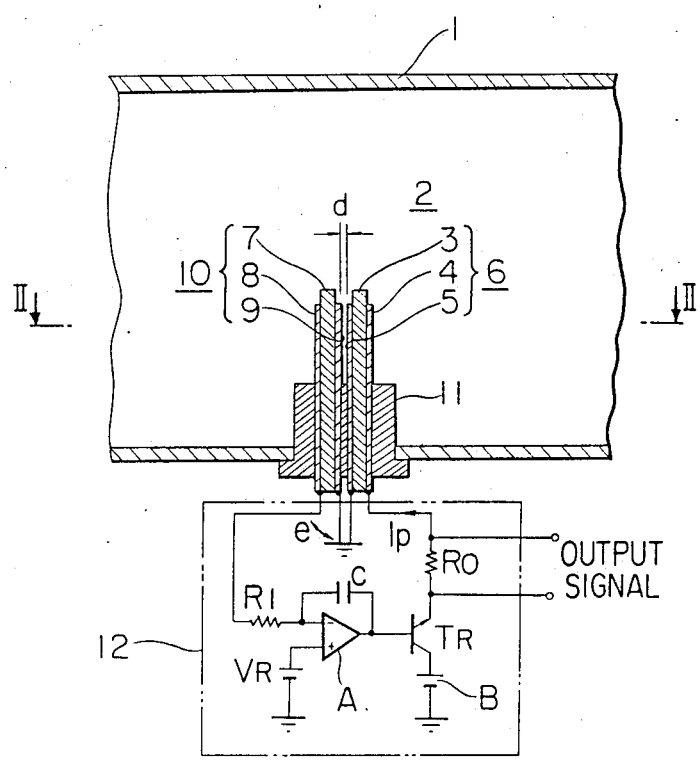
FIG. 1 is a structural view showing an embodiment of an air-to-fuel ratio sensor according to the present invention.
Figure 2:
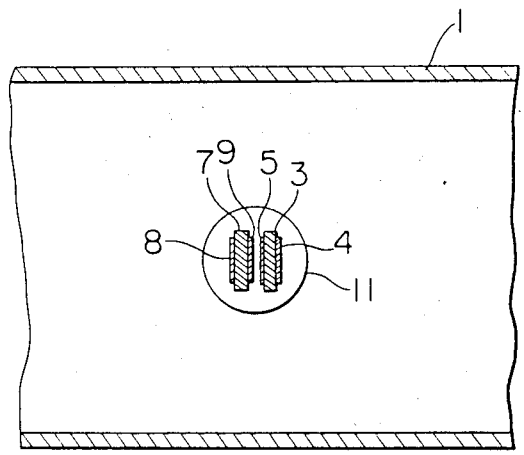
FIG. 2 is a sectional view of the sensor along the line II—II in FIG. 1.

Referring now to the drawings, reference numeral 1 designates an exhaust manifold of an engine, and reference numeral 2 designates an air-to-fuel (hereinafter referred to as A/F) ratio sensor arranged in the exhaust manifold 1. The A/F sensor 2 comprises a solid electrolyte oxygen pump 6 composed by providing platinum electrodes 4 and 5 on both side surfaces of an ionically conducting solid electrolyte (stabilized zirconia) 3, formed in the shape of a flat plate having a thickness of approx. 0.5 mm, a solid electrolyte oxygen sensor 10 composed by providing platinum electrodes 8 and 9 on both side surfaces of ionically conducting solid electrolyte 7 formed in the shape of a flat plate and constructed in the same manner as the oxygen pump 6, and a supporting base 11 for oppositely disposing the oxygen pump 6 and the oxygen sensor 10 with a small gap d of approx. 0.1 mm therebetween. Reference numeral 12 depicts an electronic control device which serves the functions of: applying an electromotive force e produced between the electrodes 8 and 9 of the oxygen sensor 10 through a resistor $R_1$ to the inverting input terminal of an operational amplifier A; driving a transistor $T_R$ by the output of the operational amplifier A by a value proportional to the difference between the electromotive force e and a reference voltage $V_R$ applied to the non-inverting input terminal of the operational amplifier A and controlling a pump current $I_P$ flowing between the electrodes 4 and 5 of the oxygen pump 6. More specifically, the electronic control device 12 serves to supply the pump current $I_P$ necessary to maintain the electromotive force e at a constant value ($V_R$). The electronic control device 12 further includes a resistor $R_0$ for producing an output signal corresponding to the pump current $I_P$ supplied from a D.C. power source B. This resistor $R_0$ is selected to be a predetermined resistance value so that the pump current $I_P$ may not flow excessively corresponding to the D.C. power source B. Reference character C designates a condenser.

Figure 3:
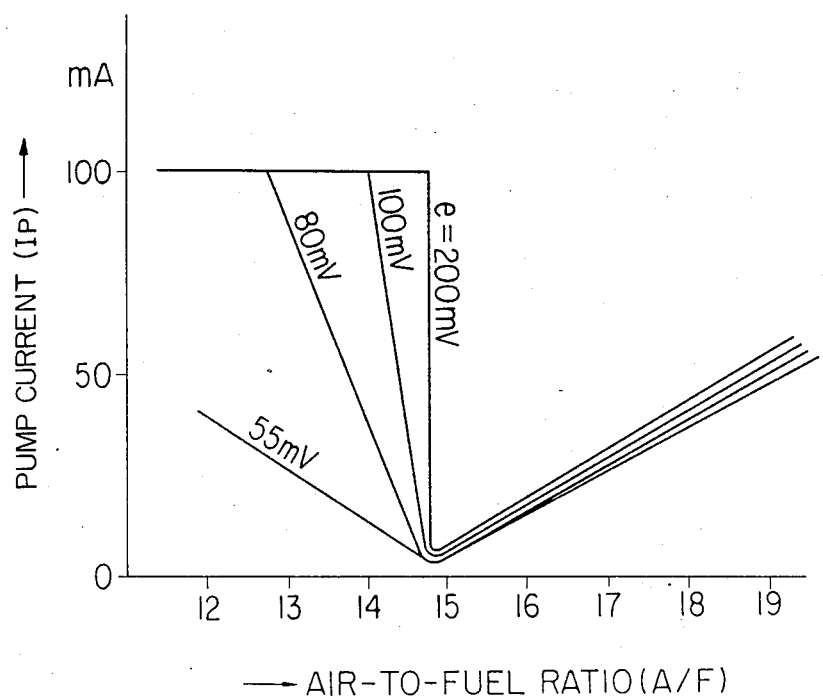
FIG. 3 is a graphical diagram showing the current of the oxygen pump when the electromotive force is altered.

The results of tests conducted with the A/F sensor of the present invention thus constructed and mounted in a gasoline engine having a 2000 cc displacement used in a Japanese automobile are shown in FIG. 3. When an excess pump current $I_P$ is caused to flow, the oxygen pump 6 is damaged. Accordingly, the pump current $I_P$ was limited by the D.C. power source B so as not to allow a current of 100 mA or higher to flow. When the electromotive force e of the oxygen sensor 10 was constantly maintained at 55 mV, the pump current $I_P$ exhibited a V-shaped curve in accordance with the variation in the air-to-fuel (A/F) ratio. When the electromotive force e was maintained constantly at 200 mV, the pump current $I_P$ abruptly altered at the stoichiometric air-to-fuel ratio, 14.7, and the pump current $I_P$ varied proportionally to the alteration in the A/F in the range that the A/F was larger than the stoichiometric A/F. The variation in the pump current $I_P$ in the vicinity of the sotichiometric A/F was less in the V-shaped characteristic in the case where the electromotive force e was maintained constantly at 55 mV, and it was difficult to accurately sense the stoichiometric A/F. Since the variation in the pump current $I_P$ was large in the characteristic in the case where the electromotive force e was maintained constantly at 200 mV, the stoichiometric A/F could be accurately detected, and a A/F larger than the stoichiometric A/F could be simultaneously sensed by an output signal corresponding to the pump current $I_P$. It was found that the electromotive force e should have been necessarily set to the voltage higher than 100 mV so as to accurately sense the stoichiometric A/F by increasing the variation in the pump current $I_P$ in the vicinity of the stoichiometric A/F as is seen in the characteristic curves in FIG. 3 in which the electromotive force e was varied. In order to more accurately sense the stoichiometric A/F, the electromotive force may be held in the range of 150 mV to 500 mV. If the electromotive force is excessively increased, a Z-shaped characteristic cannot be obtained, and the upper limit of the electromotive force is adequately 500 mV.

The reasons why the pump current $I_P$ alters proportional to the A/F in the range that the A/F is larger than the stoichiometric A/F as described above are as follows. The partial pressure of the oxygen in the exhaust gas introduced into the small gap d is altered by the operation of the oxygen pump 6, the partial pressure of the oxygen is thereby differentiated from the partial pressure of the oxygen of the exhaust gas flowing in the exhaust manifold 1, and when the pump current $I_P$ supplied to the oxygen pump 6 is controlled so that the electromotive force e of the oxygen sensor 10 generated in response to the difference between the partial pressure of the oxygen of the exhaust gas thus introduced into the small gap and the partial pressure of the oxygen of the exhaust gas flowing in the exhaust manifold 1 may become constant, and, accordingly, the control of the dispersion of the oxygen gas is carried out over a wide range by measuring the gas in the small gap d. Then, the pump current $I_P$ alters proportional to the oxygen concentration in the exhaust gas. Since the A/F is substantially proportional to the oxygen concentration, the pump current $I_P$ resultantly varies proportional to the A/F. The reason why the pump current $I_P$ alters in the range smaller than the stoichiometric A/F is considered that the A/F sensor 2 senses the carbon monoxide (CO) concentration in the exhaust gas.

What is claimed is:

1. A method of determining the air-to-fuel ratio A/F of an engine using a sensor unit mounted in an exhaust gas passage of the engine having a sensor and an oxygen pump separated by a gap, said oxygen pump comprising a solid electrolyte oxygen pump supplied with current from a source to control the partial pressure of oxygen in the gap, said sensor comprising a solid electrolyte oxygen sensor for producing an electromotive force corresponding to the difference between the partial pressure of the oxygen in the gap and the partial pressure of the oxygen in the exhaust gas flowing through the passage outside of the gap, said method comprising the steps of:

introducing exhaust gas from the passage into said gap;

controlling the current Ip to said oxygen pump so as to maintain the electromotive force produced by said oxygen sensor at a constant predetermined value of about 100 Mv to produce a mode of operation of the oxygen pump in which the magnitude of the pump current Ip as a function of the air-to-fuel ratio A/F remains substantially constant at low A/F ratios below stoichiometric A/F, changes abruptly in the vicinity of the stoichiometric A/F, and increases linearly at lean A/F ratios higher than the stoichiometric A/F and producing an output signal corresponding to the pump current Ip and detecting the air-to-fuel ratio A/F of the engine at the stoichiometric point and at lean A/F ratios by the abrupt change in the output signal occurring at the stoichiometric point and by the linear change occurring above that point.

* * * * *